United States Patent
Suzuki et al.

(10) Patent No.: US 10,786,437 B2
(45) Date of Patent: Sep. 29, 2020

(54) COMPOSITION FOR COSMETICS AND COSMETICS COMPRISING SAME

(71) Applicant: AJINOMOTO CO., INC, Tokyo (JP)

(72) Inventors: Takahiro Suzuki, Kawasaki (JP); Kazuhiko Tobita, Tokyo (JP)

(73) Assignee: AJINOMOTO CO., INC, Tokyo (JP)

( * ) Notice: Subject to any disclaimer, the term of this patent is extended or adjusted under 35 U.S.C. 154(b) by 75 days.

(21) Appl. No.: 16/170,582

(22) Filed: Oct. 25, 2018

(65) Prior Publication Data

US 2019/0060199 A1    Feb. 28, 2019

Related U.S. Application Data

(63) Continuation of application No. PCT/JP2017/016434, filed on Apr. 25, 2017.

(30) Foreign Application Priority Data

Apr. 26, 2016   (JP) .................................. 2016-088471

(51) Int. Cl.

| | |
|---|---|
| *A61K 8/44* | (2006.01) |
| *A61Q 1/02* | (2006.01) |
| *A61Q 17/04* | (2006.01) |
| *A61K 8/02* | (2006.01) |
| *A61K 8/06* | (2006.01) |

(52) U.S. Cl.
CPC .................. *A61K 8/44* (2013.01); *A61K 8/02* (2013.01); *A61K 8/06* (2013.01); *A61K 8/064* (2013.01); *A61Q 1/02* (2013.01); *A61Q 17/04* (2013.01)

(58) Field of Classification Search
CPC . A61K 8/44; A61K 8/06; A61K 8/345; A61K 8/064; A61K 8/19; A61K 8/34; A61K 8/442; A61K 8/64; A61Q 1/02; A61Q 19/10; A61Q 1/12; A61Q 5/02; A61Q 17/04; A61Q 19/00; A61Q 19/08; A61Q 1/08; A61Q 1/10; A61Q 5/12; A61Q 7/00
See application file for complete search history.

(56) References Cited

U.S. PATENT DOCUMENTS

| | | |
|---|---|---|
| 4,640,943 A | 2/1987 | Meguro et al. |
| 2003/0165448 A1 | 9/2003 | Yamato et al. |
| 2005/0287099 A1 | 12/2005 | Liechty et al. |
| 2006/0111258 A1 | 5/2006 | Tobita et al. |
| 2006/0233728 A1 | 10/2006 | Sagawa et al. |
| 2016/0000676 A1 | 1/2016 | Kuramoto et al. |

FOREIGN PATENT DOCUMENTS

| | | |
|---|---|---|
| EP | 0 139 481 A2 | 5/1985 |
| EP | 0 139 481 A3 | 5/1985 |
| EP | 0 336 265 A2 | 10/1989 |
| EP | 0 336 265 A3 | 10/1989 |
| FR | 2 785 906 A1 | 5/2000 |
| JP | 61-10503 A | 1/1986 |
| JP | 2001-10928 A | 1/2001 |
| JP | 3176712 B2 | 6/2001 |
| JP | 2003-300814 A | 10/2003 |
| JP | 2005-325123 A | 11/2005 |
| JP | 2012-153728 A | 8/2012 |
| WO | WO 2004/099121 A1 | 11/2004 |
| WO | WO 2014/142266 A1 | 9/2014 |

OTHER PUBLICATIONS

International Search Report dated Jun. 20, 2017 in PCT/JP2017/016434, 2 pages.
Extended European Search Report dated Dec. 2. 2019 in corresponding European Patent Application No. 17789561.2, 8 pages.
Anonymous: "Mattifying Finish Pressed Powder", Database GNPD [Online] MINTEL; XP055640546, Aug. 26, 2010, retrieved from www.gnpd.com, Database accession No. 1386913, 3 pages.

*Primary Examiner* — Nannette Holloman
(74) *Attorney, Agent, or Firm* — Oblon, McClelland, Maier & Neustadt, L.L.P.

(57) ABSTRACT

Compositions for cosmetics containing (A) one or more kinds of N-mono long-chain acyl basic amino acids, and (B) one or more kinds of N-mono middle-chain acyl basic amino acids, and compositions for cosmetics further containing (C) an inorganic powder, provide cosmetics that give, on application, a comfortable silky feeling and, to the skin after application, a natural translucency, good luminous finish and a uniform feeling of the skin surface, and have adhesiveness to the skin and high covering power.

14 Claims, No Drawings

COMPOSITION FOR COSMETICS AND COSMETICS COMPRISING SAME

CROSS REFERENCES TO RELATED APPLICATIONS

This application is a continuation of International Patent Application No. PCT/JP2017/016434, filed on Apr. 25, 2017, and claims priority to Japanese Patent Application No. 2016-088471, filed on Apr. 26, 2016, both of which are incorporated herein by reference in their entireties.

BACKGROUND OF THE INVENTION

Field of the Invention

The present invention relates to novel compositions for cosmetics, and cosmetics containing such a composition.

Discussion of the Background

As cosmetics containing a cosmetic powder as a main component, make-up cosmetics such as foundation, face powder, pressed powder, cheek color, eyeliner, eyebrow and the like, cosmetics for body such as body powder, baby powder and the like, and the like are commercially available. The cosmetic powder contained in these cosmetics is required to have properties giving a silky feeling to the skin, showing high uniformity and covering power, and further, showing adhesiveness and the like when applied to the skin.

Conventionally, a N-mono long-chain acyl basic amino acid represented by lauroyllysine is added as a cosmetic powder to cosmetics, and further, using same as a surface treating agent, there have been invented techniques and the like for, for example, improving attachment of the inorganic pigment to the skin, texture and the like, and hydrophobizing the hydrophilic surface thereof (see JP-A-61-10503, which is incorporated herein by reference in its entirety). N-mono long-chain acyl basic amino acids are superior in the spreadability on the skin when applying but poor in oil repellency, and therefore, defects that it decreases silky feeling of the skin after application and the like have been pointed out.

As a surface treating agent for an inorganic powder, use of N-monoacyl basic amino acid having an acyl group having 8 to 22 carbon atoms is disclosed (see U.S. Pat. No. 4,640,943, which is incorporated herein by reference in its entirety). However, combined use of a particular N-monoacyl basic amino acid having a different carbon chain length of the acyl group is not described.

Furthermore, it was proposed that a N-mono long-chain acyl basic amino acid is subjected to a surface treatment with a phosphoric acid ester ate having a specific perfluoroalkyl group to give a powder for a water- and oil-repellent cosmetic, and the powder is added to cosmetics, whereby silky feeling and moist feeling of the skin after application is improved and make-up collapse is prevented (see JP-B-3176712, which is incorporated herein by reference in its entirety). However, the feeling such as the silky feeling of the skin after application and the like are not satisfactory. Additionally, the use of the halogen type compound caused development of a new problem in the environment.

Thus, a powder for cosmetics containing N-mono long-chain acyl basic amino acid added with an α-aminolactam derivative, which can give spreadability on the skin and compatibility with the skin when applying, and silky feeling and moist feeling of the skin after application, and in consideration of the environmental aspects has been proposed (see JP-A-2012-153728, which is incorporated herein by reference in its entirety). However, a material satisfactory in both the texture such as silky feeling of the skin after application and the like, and the appearance such as natural translucency and luminous finish of appearance, uniformity of skin surface has not been obtained. In addition, sufficiently satisfactory property in terms of functions of powder such as adhesiveness to the skin and covering power has not been obtained.

Recently, moreover, provision of cosmetics superior in slipperiness, smoothness, and spreadability when applying, affording superior transparency and luminous finish feeling of the skin after application and, when pressed into the form of a solid cosmetic, superior in powder-transfer property and impact resistance and resisting the development of a glossy surface has been proposed, which is achieved by using N-mono middle-chain acyl basic amino acid powder in combination with an inorganic powder and an oil agent (see WO 2014/142266, which is incorporated herein by reference in its entirety). However, the cosmetic proposed in WO 2014/142266 gives an unpreferable slippery feeling due to low friction when applying. This in turn makes it difficult to control the power to be used for applying, and uniform feeling of the whole skin and the covering power cannot be satisfactory enough. The Examples of the afore-mentioned WO 2014/142266 do not describe a composition for cosmetics containing N-mono long-chain acyl basic amino acid and N-mono middle-chain acyl basic amino acid in combination, or a cosmetic containing the composition at a low concentration relative to that of an inorganic powder.

SUMMARY OF THE INVENTION

Accordingly, it is one object of the present invention to provide novel compositions for cosmetics that give, when applying, a comfortable silky feeling and, to the skin after application, natural translucency, good luminous finish and a uniform feeling of the skin surface, and has adhesiveness to the skin and high covering power.

It is another object of the present invention to provide novel cosmetics which contain such a composition.

These and other objects, which will become apparent during the following detailed description, have been achieved by the inventors' discovery that the object composition for cosmetics can be obtained by mixing one or more kinds of N-mono long-chain acyl basic amino acids and one or more kinds of N-mono middle-chain acyl basic amino acids. The inventors have furthermore, found that an effect similar to that of the composition can be imparted to an inorganic powder by mixing the obtained composition for cosmetics with the inorganic powder, which resulted in the completion of the present invention.

Therefore, the present invention provides the following.

(1) A composition for cosmetics, comprising (A) one or more kinds of N-mono long-chain acyl basic amino acids, and (B) one or more kinds of N-mono middle-chain acyl basic amino acids.

(2) The composition of (1), wherein a content ratio ((A):(B)) (weight ratio) of the one or more kinds of N-mono long-chain acyl basic amino acids (A) and the one or more kinds of N-mono middle-chain acyl basic amino acids (B) is 5:95 to 95:5.

(3) The composition of (1) or (2), wherein the N-mono long-chain acyl basic amino acid (A) is $N^{\epsilon}$-lauroyllysine and the N-mono middle-chain acyl basic amino acid (B) is $N^{\epsilon}$-octanoyllysine.

(4) The composition of any of (1) to (3), further comprising (C) an inorganic powder.

(5) The composition of (4), wherein a ratio of a total content of the one or more kinds of N-mono long-chain acyl basic amino acids (A) and one or more kinds of N-mono middle-chain acyl basic amino acids (B), and a content of the inorganic powder (C) (((A)+(B)):(C)) (weight ratio) is 0.5:99.5 to 99.5:0.5.

(6) The composition of (4) or (5), wherein the inorganic powder (C) is one or more kinds selected from the group consisting of silicic anhydride, silicic hydride, aluminum silicate, magnesium silicate, talc, kaolin, bentonite, mica, sericite, hydroxyapatite, aluminum oxide, magnesium oxide, light calcium carbonate, heavy calcium carbonate, light magnesium carbonate, heavy magnesium carbonate, magnesium sulfate, barium sulfate, boron nitride, zirconium oxide, zinc oxide, zinc oxide fine particles, titanium oxide, titanium oxide fine particles, titanium mica, titanium-mica coated barium sulfate, bismuth oxychloride, red iron oxide, yellow iron oxide, black iron oxide, chrome oxide, chromium hydroxide, cobalt oxide, carbon black, ultramarine blue, and iron blue.

(7) The composition of any of (4) to (6), wherein the inorganic powder (C) is one or more kinds selected from the group consisting of zinc oxide, titanium oxide and boron nitride.

(8) A cosmetic, comprising the composition of any of (1) to (7).

Advantageous Effects of Invention

The composition for cosmetics of the present invention gives, when applying to the skin, a comfortable silky feeling, can give, to the skin after application, good luminous finish and a uniform feeling of the skin surface as well as natural translucency, and has adhesiveness to the skin and high covering power.

Therefore, the cosmetics of the present invention containing the above-mentioned composition for cosmetics gives, when applying to the skin, a comfortable silky feeling, is superior in translucency, luminous finish and a uniform feeling of the skin surface after application, and is excellent in the adhesiveness to the skin and covering power.

DETAILED DESCRIPTION OF THE PREFERRED EMBODIMENTS

The composition for cosmetics of the present invention (hereinafter sometimes to be referred to as "the composition of the present invention") contains (A) one or more kinds of N-mono long-chain acyl basic amino acids and (B) one or more kinds of N-mono middle-chain acyl basic amino acids.

N-mono long-chain acyl basic amino acid contained in the composition of the present invention as component (A) is one wherein one long chain acyl group is bonded to an α-position amino group or ω-position amino group of the basic amino acid.

The basic amino acid constituting N-mono long-chain acyl basic amino acid is, for example, lysine, ornithine, 2,4-diaminobutyric acid, arginine, histidine, or the like.

Lysine is preferably used as the above-mentioned basic amino acid for the object of the present invention.

The basic amino acid used may also be any of L-form, DL-form and D-form, L-form or DL-form is preferably used, and L-form is more preferably used.

The long chain acyl group bonded to the above-mentioned basic amino acid is a saturated or unsaturated aliphatic acyl group having 12 to 22 carbon atoms, and may be linear or optionally has a branched chain. Specifically, dodecanoyl (lauroyl), tetradecanoyl(myristoyl), pentadecanoyl(pentadeciroyl), hexadecanoyl(palmitoyl), 9-hexadecenoyl(palmitoleinoyl), octadecanoyl(stearoyl), 16-methyl-heptadecanoyl (isostearoyl), cis-9-octadecenoyl(oleoyl), eicosanoyl (arachidinoyl), docosanoyl (behenoyl), and the like can be mentioned.

An acyl group having 12 to 18 carbon atoms is preferable and dodecanoyl(lauroyl) is particularly preferable for the object of the present invention.

The binding site of the above-mentioned long chain acyl group to the basic amino acid is the α-position amino group or ω-position amino group, and the α-position amino group for arginine and histidine.

Therefore, examples of the N-mono long-chain acyl basic amino acid contained in the composition of the present invention as component (A) include $N^\varepsilon$-lauroyllysine, $N^\varepsilon$-myristoyllysine, $N^\varepsilon$-palmitoyllysine, $N^\varepsilon$-stearoyllysine, $N^\varepsilon$-isostearoyllysine, $N^\varepsilon$-oleoyllysine, $N^\varepsilon$-behenoyllysine, $N^\alpha$-lauroyllysine, $N^\alpha$-myristoyllysine, $N^\alpha$-palmitoyllysine, $N^\alpha$-stearoyllysine, $N^\alpha$-isostearoyllysine, $N^\alpha$-oleoyllysine, $N^\alpha$-behenoyllyisine, $N^\delta$-lauroylornithine, $N^\delta$-palmitoylornithine, $N^\delta$-stearoylornithine, $N^\delta$-isostearoylornithine, $N^\alpha$-lauroylornithine, $N^\alpha$-palmitoylornithine, $N^\alpha$-stearoylornithine, $N^\alpha$-isostearoylornithine, $N^\gamma$-lauroyl-2,4-diaminobutyric acid, $N^\gamma$-palmitoyl-2,4-diaminobutyric acid, $N^\alpha$-lauroyl-2,4-diaminobutyric acid, $N^\alpha$-palmitoyl-2,4-diaminobutyric acid, $N^\alpha$-lauroylarginine, $N^\alpha$-palmitoylarginine, $N^\alpha$-isostearoylarginine, $N^\alpha$-lauroylhistidine, $N^\alpha$-palmitoylhistidine, $N^\alpha$-isostearoylhistidine and the like.

The N-mono long-chain acyl basic amino acid contained in the composition of the present invention as component (A) may be a free form or a salt form.

Examples of the salt of the N-mono long-chain acyl basic amino acid include alkali metal salts such as sodium salt, potassium salt and the like; alkaline earth metal salts such as magnesium salt, calcium salt and the like; inorganic acid salts such as hydrochloride, nitrate, sulfate, carbonate and the like; organic acid salts such as acetate, lactate, citrate and the like; amino acid salts such as glutamate, aspartate and the like, and the like. From the aspects of easy availability and handleability, sodium salt, potassium salt, acetate and the like are preferable.

A free form is most preferably used for the object of the present invention.

One kind of the above-mentioned N-mono long-chain acyl basic amino acid may be selected and used singly, or two or more kinds thereof may be selected and used in combination.

In the present invention, $N^\varepsilon$-lauroyllysine, particularly $N^\varepsilon$-lauroyl-L-lysine, is preferably used, since they make compatibility to the skin more preferable.

The above-mentioned (A) N-mono long-chain acyl basic amino acid either in a free form or a salt form may be prepared by protecting the α-position or ωw-position amino group in advance and according to a known production method such as Schotten-Baumann reaction including dropwise addition of fatty acid chloride and the like as described in, for example, JP-A-60-67406, which is incorporated herein by reference in its entirety, and used. Commercially available products such as "AMIHOPE LL" (manufactured by Ajinomoto Co., Inc.) and the like may also be used.

N-mono middle-chain acyl basic amino acid contained in the composition of the present invention as component (B)

is one wherein one middle chain acyl group is bonded to the α-position amino group or ω-position amino group of the basic amino acid.

The basic amino acid constituting N-mono middle-chain acyl basic amino acid and the binding site of the middle chain acyl group to the basic amino acid are the same as those in the above-mentioned N-mono long-chain acyl basic amino acid.

The middle chain acyl group bonded to the basic amino acid is a saturated or unsaturated aliphatic acyl group having 6 to 10 carbon atoms, and may be linear or optionally has a branched chain. Specifically, hexanoyl(caproyl), heptanoyl, octanoyl(capryloyl), octenoyl, 2-ethylhexanoyl, nonanoyl, decanoyl(caprinoyl), decenoyl, and the like can be mentioned.

An acyl group having 8 carbon atoms is preferable and octanoyl(capryloyl) is more preferable for the object of the present invention.

Therefore, examples of the N-mono middle-chain acyl basic amino contained in the composition of the present invention as component (B) acid include $N^\varepsilon$-hexanoyllysine, $N^\varepsilon$-octanoyllysine, $N^\varepsilon$-2-ethylhexanoyllysine, $N^\varepsilon$-decanoyllysine, $N^\varepsilon$-hexanoyllysine, $N^\alpha$-octanoyllysine, $N^\alpha$-2-ethylhexanoyllysine, $N^\alpha$-decanoyllysine, $N^\delta$-hexanoylornithine, $N^\delta$-octanoylornithine, $N^\delta$-decanoylornithine, $N^\alpha$-hexanoylornithine, $N^\alpha$-octanoylornithine, $N^\alpha$-decanoylornithine, $N^\gamma$-hexanoyl-2,4-diaminobutyric acid, $N^\gamma$-octanoyl-2,4-diaminobutyric acid, $N^\alpha$-hexanoyl-2,4-diaminobutyric acid, $N^\alpha$-octanoyl-2,4-diaminobutyric acid, $N^\alpha$-hexanoylarginine, $N^\alpha$-octanoylarginine, $N^\alpha$-hexanoylhistidine, $N^\alpha$-octanoylhistidine, and the like.

N-mono middle-chain acyl basic amino acid contained in the composition of the present invention as component (B) may also be a free form or a salt form.

Examples of the salt of the N-mono long-chain acyl basic amino acid include, as in the above-mentioned component (A), alkali metal salt, alkaline earth metal salt, inorganic acid salt, organic acid salt, amino acid salt and the like. From the aspects of easy availability and handleability, sodium salt, potassium salt, acetate and the like are preferable.

A free form is most preferably used for the object of the present invention.

One kind of the above-mentioned N-mono middle-chain acyl basic amino acid may be selected and used singly, or two or more kinds thereof may be selected and used in combination.

In the present invention, $N^\varepsilon$-octanoyllysine, particularly $N^\varepsilon$-octanoyl-L-lysine, is preferably used from the aspects of yield and operability during production.

The above-mentioned (B) N-mono middle-chain acyl basic amino acid either in a free fault or a salt form may also be prepared by a known production method such as a dehydration-condensation reaction of fatty acid and basic amino acid, as described in the above-mentioned JP-A-2012-153728, which is incorporated herein by reference in its entirety.

The content ratio of component (A) and component (B) ((A):(B)) (weight ratio) in the composition of the present invention is generally 5:95 to 95:5, preferably 10:90 to 90:10, more preferably 18:82 to 82:18.

When the content ratio of component (A) and component (B) is within the above-mentioned range, a comfortable silky feeling, natural translucency, good luminous finish and a uniform feeling of the skin surface can be given after application of the composition for cosmetics, and adhesiveness to the skin and covering power of the composition are improved.

Preferably, the composition of the present invention further contains (C) an inorganic powder.

The inorganic powder (C) contained in the composition of the present invention is not particularly limited, and inorganic powders generally used for cosmetics such as extenders, UV scattering agents, white pigments, pearlescent pigments, coloration pigments, and the like can be used.

For example, the inorganic powder used as an extender includes silicic acids such as silicic anhydride, silicic hydride and the like; silicates such as aluminum silicate, magnesium silicate and the like; clay minerals such as talc, kaolin, bentonite, mica, sericite and the like; phosphate minerals such as hydroxyapatite and the like; metal oxides such as aluminum oxide, magnesium oxide and the like; carbonates of alkaline earth metal such as light calcium carbonate, heavy calcium carbonate, light magnesium carbonate, heavy magnesium carbonate and the like; sulfates of alkaline earth metal such as magnesium sulfate, barium sulfate (platy barium sulfate, butterfly barium sulfate etc.) and the like; boron nitride and the like.

The inorganic powder used as a UV scattering agent or white pigment includes zirconium oxide, zinc oxide, zinc oxide fine particles, titanium oxide, titanium oxide fine particles and the like, and the inorganic powder used as a pearlescent pigment includes titanium mica, titanium oxide-coated barium sulfate, bismuth oxychloride and the like.

The inorganic powder used as a coloration pigment includes red iron oxide, yellow iron oxide, black iron oxide, chrome oxide, chromium hydroxide, cobalt oxide, carbon black, ultramarine blue, iron blue and the like.

One kind of the above-mentioned inorganic powder may be selected and used singly, or two or more kinds thereof may be selected and used in combination.

In the present invention, moreover, inorganic powders having fine pores such as porous silica and the like; and composite powders such as silica-coated mica, silica-coated iron oxide, acrylic resin-coated titanium mica, titanium oxide-coated talc and the like can be used as the inorganic powder (C) in addition to the above-mentioned extender and the like.

In the present invention, the above-mentioned inorganic powders subjected to a surface treatment such as silicone-treatment, fluorine compound-treatment, silane coupling agent-treatment, metal soap (aluminum stearate etc.)-treatment and the like can also be used as the inorganic powder (C).

For the object of the present invention, as the inorganic powder (C), talc, sericite, mica, zinc oxide, titanium oxide, boron nitride and the like are preferably used, zinc oxide, titanium oxide and boron nitride are more preferably used, and boron nitride is particularly preferably used since it has a hexagonal crystal layer structure and superior in lubricity.

The ratio of the total content of component (A) and component (B), and the content of component (C) (((A)+(B)):(C)) (weight ratio) in the composition of the present invention is generally 0.5:99.5 to 99.5:0.5, preferably 2:98 to 98:2, more preferably 5:95 to 95:5, further preferably 20:80 to 80:20.

The composition for cosmetics of the present invention can be produced by mixing and pulverizing component (A) and component (B) to uniformity by a mixing and pulverizing machine such as a mill mixer and the like, and the like.

When the composition for cosmetics further contains component (C), component (C) may be mixed together with component (A) and component (B), or component (A) and component (C), and component (B) and component (C) are respectively mixed and pulverized in advance, and then the mixture of component (A) and component (C), and the mixture of component (B) and component (C) are appropriately mixed and made uniform to produce the composition.

Alternatively, the composition can be produced by dissolving component (A) and component (B) by mixing in an aqueous solution of a base such as sodium hydroxide, potassium hydroxide and the like, neutralizing the mixture by adding an aqueous solution of an acid such as hydrochloric acid and the like, stirring the mixture, recovering the obtained precipitate by filtration and the like, and drying same at 40° C. to 200° C. for about 1 hr to 48 hr, preferably 50° C. to 100° C. for about 6 hr to 24 hr.

When the composition for cosmetics further contains component (C), the composition for cosmetics of the present invention can be obtained by dissolving component (C) together with component (A) and component (B) by mixing in an aqueous solution of a base, then neutralizing, stirring and recovering and drying the precipitate.

Alternatively, the composition for cosmetics of the present invention can also be obtained by respectively dissolving component (A) and component (C), and component (B) and component (C) by mixing in an aqueous solution of a base, separately neutralizing and stirring to give dried precipitates, appropriately weighing each dried product, dissolving the product by adding to and mixing in an aqueous base solution, neutralizing, stirring and drying the obtained precipitate.

The composition of the present invention containing the above-mentioned component (A) and component (B), or additionally the above-mentioned component (C) gives, when applying, a comfortable silky feeling and, to the skin after application, natural translucency, good luminous finish and a uniform feeling of the skin surface, and has good adhesiveness to the skin and high covering power.

Moreover, the present invention provides cosmetics containing the above-mentioned composition for cosmetics of the present invention (hereinafter to be also referred to as "the cosmetics of the present invention").

The cosmetics of the present invention can be used for the purpose of preparing the skin color, concealing the defects of the skin, improving the condition of the skin, for shielding UV, or for coloring on the face and lips and applying beautiful makeup. The cosmetics can take various forms such as liquid, milky, ointment, creamy, powdery or solid form or the like, preferably the form of ointment, cream, powder or solid, containing a suitable amount of powder.

Therefore, the cosmetics of the present invention is preferably provided as foundation primer such as makeup base cream and the like; make-up cosmetics such as oily ointment type foundation, oil-in-water or water-in-oil emulsion type creamy foundation, solid (cake-type) foundation, concealer, stick-type lip rouge, solid cheek color, ointment-type cheek color, stick-type cheek color, ointment-type eye color, stick-type eye color, solid eye color, solid eyeliner, solid mascara, stick-type eyebrow pencil, solid eyebrow pencil, face powder, pressed powder and the like; cosmetics for body such as body powder, baby powder and the like; sunscreen and the like.

The cosmetics of the present invention generally contains 0.1 wt % to 99.5 wt %, preferably 0.5 wt % to 99 wt %, more preferably 1 wt % to 95 wt %, of the above-mentioned composition for cosmetics of the present invention, based on the weight of the cosmetic.

Where necessary, the cosmetics of the present invention can contain, in addition to the composition for cosmetics of the present invention, oil agents such as fats and oils (e.g., olive oil, castor oil, coconut oil, cacao butter etc.), wax (e.g., Carnauba wax, candelilla wax, jojoba oil, beeswax, lanolin etc.), hydrocarbon (e.g., squalane, pristine, mineral oil, liquid paraffin, ceresin, microcrystalline wax, petrolatum etc.), fatty acid (e.g., myristic acid, palmitic acid, stearic acid, oleic acid etc.), higher alcohol (e.g., cetanol, stearyl alcohol, cetearyl alcohol, octyldodecanol etc.), ester (e.g., isopropyl myristate, isopropyl palmitate, cetyl 2-ethylhexanoate, myristic acid octyldodecyl ester, diisopropyl sebacate, lauroyl glutamate diisostearyl, lauroyl glutamate di(phytosteryl/octyldodecyl) etc.), silicone oil (e.g., octamethyltrisiloxane, methylhydrogenpolysiloxane, dimethylpolysiloxane, methylphenylpolysiloxane, decamethylcyclopentasiloxane etc.) and the like; solvents such as water, ethanol and the like; polyhydric alcohols such as propanediol, 1,3-butyleneglycol, pentyleneglycol, glycerol, sorbitol and the like; surfactants such as nonionic surfactants (e.g., glyceryl stearate, sorbitan sesquioleate, polyoxyethylene cetyl ether, polyethylene glycol monostearate, polyoxyethylene sorbitan monostearate, polyoxyethylene sorbitan monooleate etc.), anionic surfactants (e.g., sodium N-lauroyl-N-methyl-β-alanine, sodium N-lauroyl sarcosine, sodium N-stearoyl glutamate, polyoxyethylenelauryl ether sodium sulfate etc.), cationic surfactants (e.g., distearyl dimethyl ammonium chloride, stearyl trimethyl ammonium chloride etc.), amphoteric surfactants (e.g., hydrolyzed collagen.resin acid condensate etc.), silicone-based surfactants (e.g., polyoxyethylene.methylpolysiloxane copolymer etc.) and the like; oil gelation agent (e.g., N-lauroyl-L-glutamic acid dibutylamide, N-2-ethylhexanoyl-L-glutamic acid dibutylamide etc.); oil dispersing agents such as organic modified hectorite (e.g., dimethyl distearyl ammonium hectorite etc.), organic modified bentonite (e.g., dimethyl stearyl bentonite etc.); polymers (e.g., vinyl acetate.vinylpyrrolidone copolymer, polyvinylpyrrolidone, trimethylsilylpullulan etc.); metal soap (e.g., magnesium stearate, zinc stearate etc.), organic powders such as resin powders (e.g., nylon powder, crosslinking-type silicone powder etc.) and the like; humectants (e.g., panthenol, cholesterol etc.); anti-inflammatory agents (e.g., disodium succinyl glycyrrhetinate, oryzanol, bisabolol etc.); ultraviolet absorbers (e.g., 2-ethylhexyl salicylate, homomenthyl salicylate, 2-ethylhexyl paramethoxycinnamate, oxybenzone, hydroxy methoxy benzophenone sulfonate, 4-tert-butyl-4'-methoxy-dibenzoylmethane etc.); amino acids (e.g., alanine, arginine, glycine, glutamic acid, proline etc.); polyamino acid and a salt thereof (e.g., sodium poly(aspartate) etc.); vitamins such as vitamin A (e.g., retinol, retinyl palmitate etc.), vitamin B (e.g., calcium pantothenate etc.), vitamin C (e.g., sodium L-ascorbate, phosphate L-ascorbylmagnesium etc.), vitamin D (e.g., cholecalciferol etc.), vitamin E (e.g., d-δ-tocopherol, dl-α-tocopherol etc.) and the like; preservatives (e.g., sodium benzoate, phenoxyethanol, methyl paraoxybenzoate, propyl paraoxybenzoate etc.); antioxidants (e.g., tocopheryl acetate, gallic acid, dipalmitoylhydroxyproline etc.); pH adjusters (e.g., hydrochloric acid, lactic acid, citric acid, sodium hydroxide, potassium hydroxide etc.); colorants such as natural dyes (e.g., β-carotene, rutin etc.), tar pigments (e.g., Red No. 202, Blue No. 404 etc.) and the like; flavors (e.g., menthol, peppermint oil etc.) and the like.

The cosmetics of the present invention can be produced according to the form of the cosmetics, dosage form and the like by a method well known to those of ordinary skill in the art.

Oily ointment-type cosmetics can be produced, for example, as follows.

First, other powder components are added as necessary to the composition for cosmetics of the present invention and mixed. Base components such as an oil agent, a preservative, an antioxidant and the like are separately mixed and made uniform by heating melting. Thereto are added the aforementioned powder components and the mixture is kneaded by a kneader such as a roll mill and the like. Then the kneaded mixture is remelted, toned, deaerated by slowly stirring the mixture, and cooled with stirring. A flavor is added at 60° C., and the mixture is poured into a container and allowed to cool for solidification.

Creamy cosmetics can be produced, for example, as follows.

First, aqueous phase components are mixed, dissolved by heating to the uniformity of the mixture, and the mixture is heated to 75° C. Separately, oil phase components are mixed and made uniform by heating melting, the composition for cosmetics of the present invention is added and dispersed and the mixture is set to 80° C. To the aforementioned aqueous phase is added the aforementioned oil phase with stirring to allow for emulsification (oil-in-water type), or to the aforementioned oil phase is added the aforementioned aqueous phase with stirring to allow for emulsification (water-in-oil type). The emulsion is cooled by stirring, a flavor is added at 50° C., and cooled to room temperature by stirring further.

Solid (cake-type) cosmetics can be produced, for example, as follows.

Other powder components are added as necessary to the composition for cosmetics of the present invention, a colorant is added, mixed and pulverized. An oil agent as a binder, a surfactant and the like are mixed with a preservative, a flavor and the like, and the mixture is added to the aforementioned powder component and uniformly mixed. This is treated in a grinding machine, the particle sizes are adjusted by passing through a sieve, filled in a container such as a metal tray and the like and compression molded.

Powdery cosmetics can be produced, for example, as follows.

The composition for cosmetics of the present invention containing an extender such as talc and the like and a coloration pigment such as iron oxide and the like as the inorganic powder (C) is mixed in a blender, other additional components such as magnesium stearate and the like as a lubricant and the like are added, and the mixture is toned and uniformly mixed with spray of a flavor. This is passed through a grinding machine to allow for pulverization, passed through a sieve and filled in a container.

Stick-type cosmetics can be produced, for example, as follows.

Base components such as an oil agent, an antioxidant, a preservative and the like are melted by heating, and uniformly mixed. Thereto are added the composition for cosmetics of the present invention and a colorant, kneaded in a kneader such as a roll mill and the like and uniformly dispersed. Then, the mixture is remelted, a flavor is added, and the mixture is defoamed, poured into a mold, and rapidly cooled to allow for solidification. The solidified product is taken out from the mold, filled in a container and subjected to a framing treatment as necessary.

The cosmetics of the present invention containing the above-mentioned composition for cosmetics of the present invention give, when applied to the skin, a comfortable silky feeling, is superior in translucency, luminous finish and a uniform feeling of the skin surface after application, and is also excellent in the adhesiveness to the skin and covering power.

Other features of the invention will become apparent in the course of the following descriptions of exemplary embodiments which are given for illustration of the invention and are not intended to be limiting thereof.

EXAMPLES

Production Example 1. Production of N-mono Middle Chain Acyl Basic Amino Acid Powder n-Octanoic acid (manufactured by Tokyo Chemical Industry Co., Ltd.) (93.0 g) and L-lysine (manufactured by Tokyo Chemical Industry Co., Ltd.) (84.5 g) were suspended in xylene (manufactured by KANTO CHEMICAL CO., INC.) (439.2 g) at 25° C., the obtained suspension was heated to 80° C. and stirred at 80° C. for 1 hr to form an n-octane acid L-lysine salt. The suspension was further heated, water produced by the reaction was removed from the system while boiling by heating under a nitrogen atmosphere, and stirring was continued for 3 hr. After cooling, crystallized crystals were collected by filtration and the obtained crystals were washed with 516.0 g of 50 wt % aqueous ethanol solution and dried to give a white powder (139.5 g, yield 89.0%) of $N^{\varepsilon}$-octanoyl-L-lysine as the powder of Production Example 1.

Example 1. Composition for Cosmetics $N^{\varepsilon}$-lauroyl-L-lysine (5.0 g amount) and $N^{\varepsilon}$-octanoyl-L-lysine (45.0 g amount) were respectively weighed in a 100 mL Labo Milser, and mixed by the Labo Milser to give the composition for cosmetics of Example 1.

As $N^{\varepsilon}$-octanoyl-L-lysine, the powder of Production Example 1 was used and, as $N^{\varepsilon}$-lauroyl-L-lysine, commercially available "AMIHOPE LL" (manufactured by Ajinomoto Co., Inc.) was used.

Examples 2-5. Composition for Cosmetics

By a method similar to that in Example 1, $N^{\varepsilon}$-lauroyl-L-lysine, $N^{\varepsilon}$-octanoyl-L-lysine, and boron nitride ("SA08", manufactured by NIHON KOKEN KOGYO CO., LTD.) were mixed at each composition shown in Table 1 to prepare the respective compositions for cosmetics of Examples 2-5.

Example 6. Composition for Cosmetics $N^{\varepsilon}$-lauroyl-L-lysine ("AMIHOPE LL", manufactured by Ajinomoto Co., Inc.) (9.0 g amount) and $N^{\varepsilon}$-octanoyl-L-lysine (Production Example 1) (1.0 g amount) were respectively weighed in a 300 mL beaker, and dissolved by mixing in a 1.0 M aqueous sodium hydroxide solution. Thereafter, the mixture was neutralized by dropwise addition of 0.1 M hydrochloric acid at a rate of 5.0 mL/min and stirred. The obtained precipitate was recovered by filtration and dried at 60° C. overnight to give the composition for cosmetics of Example 6.

Examples 7 and 8. Composition for Cosmetics $N^{\varepsilon}$-lauroyl-L-lysine ("AMIHOPE LL", manufactured by Ajinomoto Co., Inc.), $N^{\varepsilon}$-octanoyl-L-lysine (Production Example 1), and boron nitride ("SA08", manufactured by NIHON KOKEN KOGYO CO., LTD.) were mixed at each composition shown in Table 1 to prepare the compositions for cosmetics of Examples 7 and 8.

Example 9. Composition for Cosmetics $N^{\varepsilon}$-lauroyl-L-lysine ("AMIHOPE LL", manufactured by Ajinomoto Co., Inc.) (3.0 g amount) and boron nitride ("SA08", manufactured by NIHON KOKEN KOGYO CO., LTD.) (2.0 g amount) were respectively weighed and treated in the same manner as in Example 6 to give composition (I). Furthermore, $N^\varepsilon$-octanoyl-L-lysine (Production Example 1) (13.0 g amount) and boron nitride ("SA08", manufactured by NIHON KOKEN KOGYO CO., LTD.) (2.0 g amount) were respectively weighed and treated in the same manner to give composition (II).

Then, the aforementioned composition (I) (5.0 g) and composition (II) (15.0 g) were respectively weighed and treated in the same manner as in Example 6 to give the composition for cosmetics of Example 9.

Comparative Examples 1 and 2. Powder for Cosmetics

As shown in Table 1, an $N^\varepsilon$-lauroyl-L-lysine powder ("AMIHOPE LL", manufactured by Ajinomoto Co., Inc.) was used as the powder for cosmetics of Comparative Example 1 and an $N^\varepsilon$-octanoyl-L-lysine powder (Production Example 1) was used as the powder for cosmetics of Comparative Example 2.

Example 10. Composition for Cosmetics

Untreated titanium oxide ("MT-200B", manufactured by TAYCA CORPORATION) (48.5 g amount) and the composition for cosmetics of Example 1 (1.5 g amount) were respectively weighed in a 100 mL Labo Milser, and mixed by the Labo Milser to give the composition for cosmetics of Example 10.

Examples 11-15. Composition for Cosmetics

Untreated titanium oxide ("MT-200B", manufactured by TAYCA CORPORATION) and each composition for cosmetics of Examples 2-5 and 7 were mixed at each composition shown in Table 2 to prepare the respective compositions for cosmetics of Examples 11-15 by a method similar to that in Example 10.

Comparative Examples 3 and 4. Composition for Cosmetics

Untreated titanium oxide ("MT-200B", manufactured by TAYCA CORPORATION) and each composition for cosmetics of Comparative Examples 1 and 2 were mixed at each composition shown in Table 2 to prepare the respective compositions for cosmetics of Comparative Examples 3 and 4 by a method similar to that in Example 10.

Example 16. Composition for Cosmetics

Untreated zinc oxide ("MZ-500", manufactured by TAYCA CORPORATION) (48.5 g amount) and the composition for cosmetics of Example 1 (1.5 g amount) were respectively weighed in a 100 mL Labo Milser, and mixed by the Labo Milser to give the composition for cosmetics of Example 16.

Example 17. Composition for Cosmetics

Untreated zinc oxide ("MZ-500", manufactured by TAYCA CORPORATION) and the composition for cosmetics of Example 2 were mixed at the composition shown in Table 2 to prepare the composition for cosmetics of Example 17 by a method similar to that in Example 16.

Comparative Examples 5 and 6. Composition for Cosmetics

Untreated zinc oxide ("MZ-500", manufactured by TAYCA CORPORATION) and each powder of Comparative Examples 1, 2 were mixed at each composition shown in Table 2 to prepare the respective compositions for cosmetics of Comparative Examples 5 and 6 by a method similar to that in Example 16.

Experimental Example 1. Evaluation of Sense of Use and the Like of Composition for Cosmetics The powders for cosmetics of the above-mentioned Comparative Examples 1 and 2 and respective compositions for cosmetics of Examples 1-17 and Comparative Examples 3-6 were evaluated for the silky feeling when applied to the skin, and natural translucency of the skin, luminous finish, uniform feeling and skin covering power, and adhesiveness to the skin after application by a sensual evaluation by seven professional panelists.

The compositions for cosmetics of Examples 1-9 and powders for cosmetics of Comparative Example 2 were evaluated using the powder for cosmetics of Comparative Example 1 as the comparison target, the compositions for cosmetics of Examples 10-15 and Comparative Example 4 were evaluated using the composition for cosmetics of Comparative Example 3 as the comparison target, and the compositions for cosmetics of Examples 16 and 17 and Comparative Example 6 were evaluated using the composition for cosmetics of Comparative Example 5 as the comparison target, each based on the following evaluation criteria. For each evaluation item, mean M of the evaluation points of the seven panelists was calculated and shown in Table 1 and Table 2, wherein "⊙" shows $0.5 < M \le 2.0$, "○" shows $0 < M \le 0.5$, "Δ" shows $-0.5 < M \le 0$, and "x" shows $-2.0 \le M \le -0.5$.

Evaluation Criteria (1) Silky Feeling of Skin 2 points: comfortable silky feeling as compared to the comparison target 1 point: rather comfortable silky feeling as compared to the comparison target 0 point: equal degree of silky feeling as compared to the comparison target −1 point: rather coarse or rather slippery feeling as compared to the comparison target −2 points: coarse or slippery feeling as compared to the comparison target (2) Natural Translucency of Skin 2 points: natural translucency as compared to the comparison target 1 point: rather translucent as compared to the comparison target 0 point: equal degree of translucency as compared to the comparison target −1 point: less translucency as compared to the comparison target −2 points: no translucency as compared to the comparison target (3) Luminous Finish of Skin
 2 points: high luster as compared to the comparison target
 1 point: some luster as compared to the comparison target
 0 point: equal degree of luster as compared to the comparison target
 −1 point: less luster as compared to the comparison target
 −2 points: no luster as compared to the comparison target
(4) Uniform Feeling of Skin
 2 points: highly uniform feeling as compared to the comparison target
 1 point: rather uniform feeling as compared to the comparison target
 0 point: equal degree of uniform feeling as compared to the comparison target
 −1 point: some light and shade of skin as compared to the comparison target
 −2 points: light and shade of skin as compared to the comparison target
(5) Covering Power of Skin
 2 points: high covering power as compared to the comparison target
 1 point: some covering power as compared to the comparison target
 0 point: equal degree of covering power as compared to the comparison target
 −1 point: rather less covering power as compared to the comparison target
 −2 points: no covering power as compared to the comparison target
(6) Adhesiveness to Skin
 2 points: very high adhesiveness as compared to the comparison target
 1 point: rather high adhesiveness as compared to the comparison target
 0 point: equal degree of adhesiveness as compared to the comparison target
 −1 point: rather floats off as compared to the comparison target
 −2 points: floats off as compared to the comparison target

TABLE 1

| | components | Comp. Ex. 1 | Ex. 1 | Ex. 2 | Ex. 3 | Ex. 4 | Ex. 5 | Ex. 6 | Ex. 7 | Ex. 8 | Ex. 9 | Comp. Ex. 2 |
|---|---|---|---|---|---|---|---|---|---|---|---|---|
| (A) | $N^\varepsilon$-lauroyl-L-lysine | 100 | 90 | 65 | 33.3 | 15 | 10 | 90 | 65 | 15 | 15 | 0 |
| (B) | $N^\varepsilon$-octanoyl-L-lysine | 0 | 10 | 15 | 33.3 | 65 | 90 | 10 | 15 | 65 | 65 | 100 |
| (C) | boron nitride | 0 | 0 | 20 | 33.3 | 20 | 0 | 0 | 20 | 20 | 20 | 0 |
| | total amount (g) | 100 | 100 | 100 | 100 | 100 | 100 | 100 | 100 | 100 | 100 | 100 |
| evaluation item | silky feeling | — | ⊙ | ⊙ | ⊙ | ⊙ | ⊙ | ⊙ | ⊙ | ⊙ | ⊙ | △ |
| | natural translucency | — | ○ | ⊙ | ⊙ | ⊙ | ⊙ | ○ | ⊙ | ⊙ | ⊙ | ○ |
| | luminous finish | — | ○ | ⊙ | ⊙ | ⊙ | ⊙ | ○ | ⊙ | ⊙ | ⊙ | △ |
| | uniform feeling of skin | — | ⊙ | ⊙ | ⊙ | ⊙ | ⊙ | ⊙ | ⊙ | ⊙ | ⊙ | ○ |
| | covering power | — | ○ | ⊙ | ⊙ | ⊙ | ○ | ○ | ⊙ | ⊙ | ⊙ | △ |
| | adhesiveness | — | ⊙ | ⊙ | ⊙ | ⊙ | ○ | ⊙ | ⊙ | ⊙ | ⊙ | X |

TABLE 2

| | components | Comp. Ex. 3 | Comp. Ex. 4 | Ex. 10 | Ex. 11 | Ex. 12 | Ex. 13 | Ex. 14 | Ex. 15 | Comp. Ex. 5 | Comp. Ex. 6 | Ex. 16 | Ex. 17 |
|---|---|---|---|---|---|---|---|---|---|---|---|---|---|
| (C) | titanium oxide | 97 | 97 | 97 | 97 | 97 | 97 | 97 | 97 | | | | |
| | zinc oxide | | | | | | | | | 97 | 97 | 97 | 97 |
| powder | Comp. Ex. 1 | 3 | | | | | | | | 3 | | | |
| | Comp. Ex. 2 | | 3 | | | | | | | | 3 | | |
| composition for cosmetics | Example 1 | | | 3 | | | | | | | | 3 | |
| | Example 2 | | | | 3 | | | | | | | | 3 |
| | Example 3 | | | | | 3 | | | | | | | |
| | Example 4 | | | | | | 3 | | | | | | |
| | Example 5 | | | | | | | 3 | | | | | |
| | Example 7 | | | | | | | | 3 | | | | |
| | total amount (g) | 100 | 100 | 100 | 100 | 100 | 100 | 100 | 100 | 100 | 100 | 100 | 100 |
| evaluation item | silky feeling | — | △ | ⊙ | ⊙ | ⊙ | ⊙ | ⊙ | ⊙ | — | △ | ⊙ | ⊙ |
| | natural translucency | — | ○ | ○ | ⊙ | ⊙ | ⊙ | ⊙ | ⊙ | — | ○ | ○ | ⊙ |
| | luminous finish | — | ○ | ⊙ | ⊙ | ⊙ | ⊙ | ⊙ | ⊙ | — | ○ | ⊙ | ⊙ |
| | uniform feeling of skin | — | △ | ⊙ | ⊙ | ⊙ | ⊙ | ⊙ | ⊙ | — | △ | ⊙ | ⊙ |
| | covering power | — | △ | ⊙ | ⊙ | ⊙ | ⊙ | ⊙ | ⊙ | — | △ | ⊙ | ⊙ |
| | adhesiveness | — | △ | ⊙ | ⊙ | ⊙ | ⊙ | ⊙ | ⊙ | — | △ | ⊙ | ⊙ |

As shown in Table 1, the respective compositions for cosmetics of Examples 1-9 of the present invention were evaluated to be good ("⊙") or rather good ("○") in silky feeling when applied to the skin, and natural translucency, luminous finish, uniform feeling of skin after application, and covering power and adhesiveness as compared to the powder for cosmetics of Comparative Example 1 ((A) $N^\varepsilon$-lauroyl-L-lysine powder). Particularly, the compositions for cosmetics of Examples 2-4 and 7-9 containing (A) $N^\varepsilon$-lauroyl-L-lysine and (B) $N^\varepsilon$-octanoyl-L-lysine at a weight ratio ((A):(B)) of 4.3:1 to 1:4.3 and further containing (C) boron nitride at a weight ratio ((A)+(B)):(C) of 4:1 to 2:1 were evaluated to be good ("⊚") in all evaluation items as compared to the powder of Comparative Example 1.

On the other hand, the $N^\varepsilon$-octanoyl-L-lysine powder (B) of Comparative Example 2 was evaluated to be rather good ("○") in natural translucency and uniform feeling after application to the skin as compared to the powder for cosmetics of Comparative Example 1; however, it was evaluated to be bad ("x") in the adhesiveness to the skin.

As shown in Table 2, moreover, the compositions for cosmetics of Examples 10-17, that were mixtures of 3 parts by weight each of the compositions for cosmetics of Examples 1-5, 7 of the present invention and untreated titanium oxide or zinc oxide (97 parts by weight) were also evaluated to be good ("⊚") or rather good ("○") in silky feeling when applied to the skin, and natural translucency, luminous finish, uniform feeling of skin after application, and covering power and adhesiveness to the skin as compared to the composition for cosmetics as the comparison target.

In contrast, the composition for cosmetics of Comparative Example 4, which was a mixture of the powder for cosmetics of Comparative Example 2 and titanium oxide, and the composition for cosmetics of Comparative Example 6, which was a mixture of the powder for cosmetics of Comparative Example 2 and zinc oxide, were evaluated to be not much different ("Δ") except in natural translucency and luminous finish of skin after application that were evaluated to be rather good ("○") as compared to the respective compositions for cosmetics of Comparative Examples 3 and 5, that were mixtures of the powder for cosmetics of Comparative Example 1 and each of titanium oxide and zinc oxide.

Example 18. Solid Foundation

According to the formulation shown in Table 3, a solid foundation was produced as in the following.

Production method: In Table 3, components (A)-(C) were mixed, an organic powder was added, mixed and pulverized. An oil agent, a preservative and an antioxidant were mixed and added to the aforementioned powder component, uniformly mixed, and pulverization-treated in a grinding machine. The particle sizes were adjusted by passing the mixture through a sieve, and the mixture was filled in a metal tray and compression molded.

TABLE 3

| | components | content (wt %) |
|---|---|---|
| (A) | $N^\varepsilon$-lauroyl-L-lysine | 5.00 |
| (B) | $N^\varepsilon$-octanoyl-L-lysine | 5.00 |
| (C) | silicone-treated talc | 5.40 |
| | silicone-treated mica | 32.00 |
| | silicone-treated sericite | 20.00 |
| | silicone-treated titanium oxide | 8.00 |
| | aluminum stearate-treated titanium oxide | 3.00 |
| | silicone-treated zinc oxide | 2.00 |
| | silicone-treated red iron oxide | 0.40 |
| | silicone-treated yellow iron oxide | 1.00 |
| | silicone-treated black iron oxide | 0.15 |
| | boron nitride | 5.00 |

TABLE 3-continued

| | components | content (wt %) |
|---|---|---|
| organic powder | nylon powder | 2.00 |
| oil agent | dimethylpolysiloxane | 4.98 |
| | diglyceryl isostearate | 3.00 |
| | N-myristoyl-N-methyl-β-alanine(phytosteryl/decyltetradecyl) | 1.00 |
| | mineral oil | 2.00 |
| preservative | methyl paraoxybenzoate | 0.06 |
| antioxidant | tocopherol | 0.01 |
| | total | 100.0 |

Example 19. Loose Powder Foundation

According to the formulation shown in Table 4, a loose powder foundation was produced as in the following.

Production method: In Table 4, components (A)-(C) were mixed and pulverized. An oil agent, a preservative and an antioxidant were mixed and added to the aforementioned powder component, uniformly mixed, and pulverization-treated in a grinding machine. The particle sizes were adjusted by passing the mixture through a sieve, and the mixture was filled in a metal tray.

TABLE 4

| | components | content (wt %) |
|---|---|---|
| (A) | $N^\varepsilon$-lauroyl-L-lysine | 8.00 |
| (B) | $N^\varepsilon$-octanoyl-L-lysine | 2.00 |
| (C) | silicone-treated talc | 5.00 |
| | silicone-treated mica | 54.90 |
| | titanium oxide | 18.00 |
| | aluminum stearate-treated titanium oxide | 3.00 |
| | silicone-treated red iron oxide | 0.60 |
| | silicone-treated yellow iron oxide | 1.50 |
| | silicone-treated black iron oxide | 0.30 |
| | porous silica | 0.50 |
| | boron nitride | 5.00 |
| oil agent | glyceryl tri(2-ethylhexanoate) | 0.59 |
| | N-lauroyl glutamate di(phytosteryl/octyldodecyl) | 0.20 |
| | N-lauroylsarcosine isopropyl | 0.20 |
| preservative | methyl paraoxybenzoate | 0.20 |
| antioxidant | tocopherol | 0.01 |
| | total | 100.0 |

Example 20. Sunscreen

According to the formulation shown in Table 5, a sunscreen was produced as in the following.

Production method: In Table 5, an oil agent, a surfactant and an antioxidant were mixed, melted by heating, (A)-(C) were added and dispersed and the dispersion was heated to 80° C. to give an oil phase. On the other hand, a humectant, polyhydric alcohol, a water-soluble polymer and a preservative were added to water, mixed and dissolved by heating to 75° C. to give an aqueous phase. The aforementioned oil phase was added to the aforementioned aqueous phase with stirring for emulsification and then the emulsion was cooled with stirring to room temperature.

TABLE 5

| | components | content (wt %) |
|---|---|---|
| oil agent | dimethylpolysiloxane | 4.0 |
| | decamethylcyclopentasiloxane | 15.0 |
| | N-lauroyl glutamate di(octyldodecyl/phytosteryl/behenyl) | 1.0 |
| surfactant | polyoxyethylene · methylpolysiloxane copolymer | 2.0 |
| antioxidant | tocopheryl acetate | 0.1 |
| (A) | N$^\varepsilon$-lauroyl-L-lysine | 3.0 |
| (B) | N$^\varepsilon$-octanoyl-L-lysine | 3.0 |
| (C) | titanium oxide fine particles | 5.0 |
| | zinc oxide | 10.0 |
| | magnesium sulfate | 0.5 |
| humectant | sodium pyrrolidonecarboxylate (50 wt % aqueous solution) | 0.5 |
| polyhydric alcohol | glycerol | 5.0 |
| | 1,3-butyleneglycol | 5.0 |
| water-soluble polymer | hydroxyethylcellulose | 0.1 |
| preservative | phenoxyethanol | 0.3 |
| solvent | water | 45.5 |
| | total | 100.0 |

Example 21. Liquid Foundation

According to the formulation shown in Table 6, a liquid foundation was produced as in the following.

Production method: In Table 6, an oil agent, a surfactant, an ultraviolet absorber, an oil dispersing agent and a moisturizer were mixed, melted by heating, (A)-(C) were added and dispersed and the dispersion was heated to 80° C. to give an oil phase. On the other hand, polyhydric alcohol and a preservative were added to water, mixed and dissolved by heating to 75° C. to give an aqueous phase. The aforementioned oil phase was added to the aforementioned aqueous phase with stirring for emulsification and then the emulsion was cooled with stirring to 50° C., ethanol was added and the mixture was further cooled to room temperature.

TABLE 6

| | components | content (wt %) |
|---|---|---|
| oil agent | octamethylcyclotetrasiloxane | 17.0 |
| | cetyl octanate | 6.0 |
| | N-lauroyl glutamate di(cholesteryl/behenyl/octyldodecyl) | 2.0 |
| surfactant | polyoxyethyleneglyceryl triisostearate | 5.0 |
| | triglyceryl diisostearate | 1.5 |
| UV absorber | 2-ethylhexyl para-methoxycinnamate | 2.0 |
| | 4-tert-butyl-4'-methoxydibenzoylmethane | 1.0 |
| oil dispersing agent | dimethyl stearyl bentonite | 0.5 |
| humectant | sodium acetylethylcarboxylmethylthiazolidine-carboxylate | 2.0 |
| (A) | N$^\varepsilon$-lauroyl-L-lysine | 1.0 |
| (B) | N$^\varepsilon$-octanoyl-L-lysine | 3.0 |
| (C) | boron nitride | 1.0 |
| | titanium oxide | 11.0 |
| | talc | 6.0 |
| | silicone-treated red iron oxide | 1.2 |
| | silicone-treated yellow iron oxide | 3.0 |
| | silicone-treated black iron oxide | 0.6 |

TABLE 6-continued

| | components | content (wt %) |
|---|---|---|
| polyhydric alcohol | 1,3-butyleneglycol | 5.0 |
| preservative | methyl paraoxybenzoate | 0.2 |
| solvent | ethanol | 7.0 |
| | water | 24.0 |
| | total | 100.0 |

Example 22. Sunscreen Cream

According to the formulation shown in Table 7, a sunscreen cream was produced as in the following.

Production method: In Table 7, an oil agent, a surfactant, an ultraviolet absorber and an antioxidant were mixed, melted by heating, (A)-(C) were added and dispersed and the dispersion was heated to 80° C. to give an oil phase. On the other hand, polyhydric alcohol, a water-soluble polymer, a preservative and a base were added to water, mixed and dissolved by heating to 75° C. to give an aqueous phase. The aforementioned oil phase was added to the aforementioned aqueous phase with stirring for emulsification and then the emulsion was cooled with stirring to room temperature.

TABLE 7

| | components | content (wt %) |
|---|---|---|
| oil agent | tri(capryl/capric acid)glyceryl | 10.0 |
| | ethylhexyl dimethoxy benzylidene dioxoimidazolidinepropionic acid | 2.0 |
| | stearic acid | 0.5 |
| | cetanol | 0.5 |
| | dimethylpolysiloxane | 2.0 |
| surfactant | sorbitan stearate | 2.0 |
| | polyoxyethylene (20E.O.) sorbitan monostearate | 1.0 |
| UV absorber | 2-ethylhexyl para-methoxycinnamate | 8.0 |
| antioxidant | tocopheryl acetate | 0.1 |
| (A) | N$\varepsilon$-lauroyl-L-lysine | 1.0 |
| (B) | N$\varepsilon$-octanoyl-L-lysine | 1.0 |
| (C) | aluminum stearate-treated titanium oxide | 6.0 |
| polyhydric alcohol | 1,3-butyleneglycol | 5.0 |
| water-soluble polymer | carboxyvinyl polymer (0.5 wt % aqueous solution) | 36.0 |
| preservative | methyl paraoxybenzoate | 0.2 |
| base | sodium hydroxide (1 wt % aqueous solution) | 3.6 |
| solvent | water | 21.1 |
| | total | 100.0 |

Example 23. Water-in-Oil Emulsion Foundation

According to the formulation shown in Table 8, a water-in-oil emulsion foundation was produced as in the following.

Production method: In Table 8, an oil agent, a surfactant, an oil dispersing agent and an ultraviolet absorber were mixed, melted by heating, (A)-(C) and an organic powder were added and dispersed and the dispersion was heated to 80° C. to give an oil phase. On the other hand, polyhydric alcohol, a thickener (sodium chloride) and a preservative were added to a part of water, mixed and dissolved by heating to 75° C. to give an aqueous phase. The aforementioned aqueous phase was added to the aforementioned oil phase with stirring for emulsification and then the emulsion was cooled with stirring. Polyamino acid salt and amino acid were dissolved in the rest of the water at 40° C. and added, then an oil agent (hexamethyldisiloxane) and a flavor were added, and the mixture was further cooled to room temperature. Finally, a crosslinked silicone powder dispersion was added and homogeneously dispersed by a homogenizer.

TABLE 8

| | components | content (wt %) |
|---|---|---|
| oil agent | cyclopentasiloxane | 3.00 |
| | dimethylpolysiloxane | 4.00 |
| | cetyl 2-ethylhexanoate | 4.00 |
| surfactant | sodium N-stearoyl glutamate | 5.00 |
| | diglyceryl dipolyhydroxystearate | 4.00 |
| oil dispersing agent | dimethyl distearyl ammonium hectorite | 5.00 |
| ultraviolet absorber | 2-ethylhexyl (RS)-2-cyano-3,3-diphenylpropa-2-enoic acid | 3.00 |
| | 4-tert-butyl-4'-methoxydibenzoylmethane | 2.00 |
| | 2-ethylhexyl para-methoxycinnamate | 8.00 |
| | 2-ethylhexyl salicylate | 4.00 |
| (A) | $N^\varepsilon$-lauroyl-L-lysine | 0.50 |
| (B) | $N^\varepsilon$-octanoyl-L-lysine | 1.50 |
| (C) | silicone-treated red iron oxide | 0.60 |
| | silicone-treated yellow iron oxide | 0.15 |
| | silicone-treated black iron oxide | 0.20 |
| | silicone-treated talc | 3.00 |
| | silicone-treated mica | 3.00 |
| | silicone-treated titanium oxide | 5.00 |
| | boron nitride | 1.00 |
| organic powder | nylon powder | 1.00 |
| polyhydric alcohol | glycerol | 1.50 |
| | 1,3-butyleneglycol | 1.00 |
| thickener | sodium chloride | 1.00 |
| polyamino acid salt | sodium poly(aspartate) (30 wt % aqueous solution) | 3.00 |
| amino acid | arginine | 0.01 |
| | glutamic acid | 0.01 |
| | proline | 0.01 |
| | glycine | 0.01 |
| | alanine | 0.01 |
| preservative | methyl paraoxybenzoate | 0.30 |
| oil agent | hexamethyldisiloxane | 6.00 |
| flavor | flavor | 0.20 |
| solvent | water | 24.00 |
| crosslinked silicone powder dispersion | (vinyldimethyl/trimethylsiloxysilicic acid/dimethylpolysiloxane) crosslinked polymer (dimethylpolysiloxane dispersion) | 5.00 |
| | total | 100.00 |

INDUSTRIAL APPLICABILITY

As described in detail above, the present invention can provide a composition for cosmetics that gives, when applying, a comfortable silky feeling and, to the skin after application, natural translucency, good luminous finish and a uniform feeling of the skin surface, and has adhesiveness to the skin and high covering power.

Furthermore, by containing the above-mentioned composition for cosmetics of the present invention, cosmetics that give, when applying to the skin, a comfortable silky feeling, are superior in natural translucency, luminous finish and a uniform feeling of the skin surface after application, and are also excellent in the adhesiveness to the skin and covering power can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition for cosmetics, comprising:
   (A) one or more N-mono long-chain acyl basic amino acid having an acyl group having 12 to 22 carbon atoms; and
   (B) one or more N-mono middle-chain acyl basic amino acid having an acyl group having 6 to 10 carbon atoms, wherein said one or more N-mono long-chain acyl basic amino acid (A) and said one or more N-mono middle-chain acyl basic amino acid (B) are present in a weight ratio ((A):(B)) of 18:82 to 82:18.

2. The composition according to claim 1, wherein said one or more N-mono long-chain acyl basic amino acid (A) comprises $N^\varepsilon$-lauroyllysine and said one or more N-mono middle-chain acyl basic amino acid (B) comprises $N^\varepsilon$-octanoyllysine.

3. The composition according to claim 1, further comprising
   (C) at least one inorganic powder.

4. The composition according to claim 3, wherein said one or more N-mono long-chain acyl basic amino acid (A), said one or more N-mono middle-chain acyl basic amino acid (B), and said at least one inorganic powder (C) are present in a weight ratio of a total content of said one or more N-mono long-chain acyl basic amino acid (A) and said one or more N-mono middle-chain acyl basic amino acid (B), to a content of said at least one inorganic powder (C) (((A)+(B)):(C)) of 0.5:99.5 to 99.5:0.5.

5. The composition according to claim 3, wherein said at least one inorganic powder (C) comprises one or more powders selected from the group consisting of silicic anhydride, silicic hydride, aluminum silicate, magnesium silicate, talc, kaolin, bentonite, mica, sericite, hydroxyapatite, aluminum oxide, magnesium oxide, light calcium carbonate, heavy calcium carbonate, light magnesium carbonate, heavy magnesium carbonate, magnesium sulfate, barium sulfate, boron nitride, zirconium oxide, zinc oxide, zinc oxide fine particles, titanium oxide, titanium oxide fine particles, titanium mica, titanium-mica coated barium sulfate, bismuth oxychloride, red iron oxide, yellow iron oxide, black iron oxide, chrome oxide, chromium hydroxide, cobalt oxide, carbon black, ultramarine blue, and iron blue.

6. The composition according to claim 4, wherein said at least one inorganic powder (C) comprises one or more powders selected from the group consisting of silicic anhydride, silicic hydride, aluminum silicate, magnesium silicate, talc, kaolin, bentonite, mica, sericite, hydroxyapatite, aluminum oxide, magnesium oxide, light calcium carbonate, heavy calcium carbonate, light magnesium carbonate, heavy magnesium carbonate, magnesium sulfate, barium sulfate, boron nitride, zirconium oxide, zinc oxide, zinc oxide fine particles, titanium oxide, titanium oxide fine particles, titanium mica, titanium-mica coated barium sulfate, bismuth oxychloride, red iron oxide, yellow iron oxide, black iron oxide, chrome oxide, chromium hydroxide, cobalt oxide, carbon black, ultramarine blue, and iron blue.

7. The composition according to claim 3, wherein said at least one inorganic powder (C) comprises one or more powders selected from the group consisting of zinc oxide, titanium oxide, and boron nitride.

8. The composition according to claim 4, wherein said at least one inorganic powder (C) comprises one or more powders selected from the group consisting of zinc oxide, titanium oxide, and boron nitride.

9. A cosmetic, comprising a composition according to claim 1.

10. The cosmetic according to claim 9 which is a solid foundation.

11. The cosmetic according to claim 9 which is loose powder foundation.

12. The cosmetic according to claim 9 which is a sunscreen.

13. The cosmetic according to claim 9 which is a liquid foundation.

14. The cosmetic according to claim 9 which is a water-in-oil emulsion foundation.

* * * * *